United States Patent [19]

Ngo et al.

[11] Patent Number: 5,196,536

[45] Date of Patent: Mar. 23, 1993

[54] 2-FLUORO-1-METHYLPYRIDINIUM SALT ACTIVATED DIOLS AND POLYOLS AS CROSS-LINKERS

[75] Inventors: That T. Ngo, Irvine; Faizy Ahmed, Anaheim, both of Calif.

[73] Assignee: UniSyn Fibertec Corporation, Tustin, Calif.

[21] Appl. No.: 869,507

[22] Filed: Apr. 16, 1992

Related U.S. Application Data

[62] Division of Ser. No. 404,930, Sep. 8, 1989, Pat. No. 5,130,436.

[51] Int. Cl.$^5$ ............................................. C07D 213/64
[52] U.S. Cl. .................................... 546/261; 564/152; 564/153; 564/159; 568/38; 568/44; 568/57
[58] Field of Search ..................... 564/152, 153, 159; 568/38, 44, 57; 546/261

[56] References Cited

PUBLICATIONS

Ngo, T. T., Biotechnology 4:134 (1986).

Primary Examiner—Marianne M. Cintins
Assistant Examiner—John Peabody
Attorney, Agent, or Firm—Edward S. Irons

[57] ABSTRACT

A novel class of cross-linking agent, which comprises a monomeric organic compound having at least two hydroxyl groups each bonded to a different carbon atom, wherein said hydroxyl groups are activated by reaction with 2-fluoro-1-methylpyridinium toluene-4-sulfonate (FMP). Suitable monomeric organic compounds include diols and polyols. Such cross-linking agents may be conveniently prepared by reaction of the monomeric organic compound with FMP in a suitable solvent, followed by recovery of the resultant reaction products, e.g., via precipitation and filtration. The novel cross-linking agents have a wide variety of uses, including the interconnection of subunits of multimeric enzymes and the covalent immobilization of organic ligands to suitable carriers or supports.

6 Claims, 3 Drawing Sheets

2-FLUORO-1-METHYLPYRIDINIUM SALT ACTIVATED DIOLS AND POLYOLS AS CROSS-LINKERS

This is a division of application Ser. No. 07/404,930 filed Sep. 8, 1989, U.S. Pat. No. 5,130,436.

FIELD OF THE INVENTION

This invention relates to compositions and methods for use in covalently binding two or more organic molecules with each other. In one of its more particular aspects, this invention relates to methods and compositions for use in cross-linking proteinaceous materials to one another and/or to non-proteinaceous materials, such as polymeric solid supports.

BACKGROUND OF THE INVENTION

Chemical cross-linkers are compounds which have the ability to covalently link two or more molecules with each other. Cross-linkers are used, e.g., to link protein molecules to one another, proteins to nucleic acids, carbohydrates to proteins or carbohydrates to other carbohydrates. The agents can also be used for the covalent attachment of proteins, nucleic acids or other small molecules to solid supports for their immobilization. These chemical cross-linker compounds have generally been symmetrically bifunctional in nature and can be further subdivided into three major classes: (1) homobifunctional reactive cross-linkers which contain the same reactive group on both ends of the molecule (X-X); (2) heterobifunctional reactive cross-linkers which have different reactive groups in their structure (X-Y), the reactive groups X and Y usually having different chemical specificities toward functional group(s) on the molecule(s) to be cross-linked; and (3) cleavable cross-linkers which contain in their structure one or more functional groups which can be cleaved under controlled conditions and which can either be homo- or heterobifunctional in nature.

A wide range of chemical cross-linkers have heretofore been developed. Representative homobifunctional cross-linkers (X-X) include bisactivated esters, bisimidates, alkylating agents, diazides, dialdehydes, triazines and benzoquinone. Heterobifunctional cross-linkers (X-Y) employed to date generally incorporate in their structures a combination of the reactive groups mentioned above. For example, combinations of acylating and alkylating groups or acylating and photoactivatable functionalities have been employed in this class of cross-linkers. Cleavable cross-linkers (either homo- or heterobifunctional) have metastable bonds that can be cleaved under controlled conditions, such as by using mild chemical treatment. The most widely employed metastable functionalities in cross-linkers are disulfides (which can be cleaved in the presence of free sulfhydryls) and vicinal hydroxyls (which can be cleaved by sodium periodate oxidation under mild conditions).

Cross-linking agents have a wide range of chemical and biochemical applications. These can be broadly classified into three categories: (1) cross-linking soluble compounds; (2) attaching soluble compounds to solid surfaces; and (3) cross-linking synthetic polymers (such as used in chromatographic methods) in order to improve their mechanical strength.

Cross-linkers have been extensively used to study the quaternary structure of multi-subunit proteins and to investigate spatial relationships of subunits and their interaction within the proteins. Both homo- and heterobifunctional cross-linkers have also found widespread applications in the preparation and use of immunodiagnostic reagents. For example, in enzyme linked immunosorbant assays (ELISA), the enzyme label is covalently linked through the use of a cross-linker to a hapten, antigen or antibody. Similarly, non-enzymatic labels can also be attached using such cross-linkers. Conjugation of a toxin to a specific antibody in the preparation of immunotoxin can be achieved by using such reagents. Attachment of nonimmunogenic polymers, such as poly(ethylene glycol), to a protein via bifunctional cross-linkers may result in a conjugate molecule that can evoke immune tolerance.

Using the same principles of cross-linking, it is possible to covalently attach proteins, nucleic acids or other ligands to a solid surface using cross-linking agents. For example, a solid surface containing a suitable functional group can attach itself to one end of a cross-linker. The other end of the cross-linker can then react with a functional group on the protein which can thus covalently attach itself to the solid support.

Many of the known cross-linking reagents have serious disadvantages, limiting their practical use. For a cross-linking reaction to be complete, the reagent should have a reasonable half-life in the buffer system or other medium used; in other words, the rate of hydrolysis of the reagent must be sufficiently slow that the reagent is available for the period of time necessary for the cross-linking reaction to be substantially completed. However, this is not the case with respect to certain reagents; for example, the half-life of bisimidates is about 4 minutes under acidic or slightly alkaline conditions (pH 8.0). In general, cross-linking reactions are carried out at a pH of 8.5; consequently, one must either keep adding reagent to compensate for losses due to hydrolysis until the desired cross-linking reaction is complete, or use a much higher pH with addition of reagent during reaction to facilitate cross-linking (i.e., pH 10.0 or above). Most proteins and nucleic acids are not stable at these pH levels. Moreover, some of the cross-linkers described above also suffer from problems of poor solubility in the types of solvent which would most commonly be employed with the materials it is desired to cross link.

2-fluoro-1-methylpyridinium toluene-4-sulfonate (FMP) has heretofore been used in the activation of hydroxyl functions on solid supports, generally polymeric in nature and containing a plurality of hydroxyl groups (Ngo, T. T., "Facile Activation of Sepharose Hydroxyl Groups by 2-Fluoro-1-Methylpyridinium Toluene-4-Sulfonate: Preparation of Affinity and Covalent Chromatography Matrices," Biotechnology 4: 134 (1986)). The thus-activated support contains 2-alkoxy-1-methylpyridinium groups bound to its surface. This chemical entity can easily be displaced as 1-methyl-2-pyridone by nucleophiles (such as primary amino or sulfhydryl groups) from another molecule, thereby resulting in the covalent attachment of the nucleophile to the solid support.

Thus, U.S. Pat. No. 4,582,875 describes a method for preparing a stable and hydrolysis-resistant coupling product of a polymeric gel and an organic ligand, in which the organic ligand is covalently bonded directly to a carbon atom in the polymeric gel. According to this patent, a reactive derivative of a polymeric hydroxyl-containing gel is formed by reacting the gel with 2-fluoro-1-methylpyridinium toluene-4-sulfonate (FMP)

and then reacting the activated carrier with a ligand containing a primary amino acid or sulfhydryl group. The patent is directed to activation of hydroxyl groups of polymeric substances containing at least one hydroxyl group; specific examples of such polymeric substrates include polysaccharides, poly(ethylene glycol), poly(vinyl alcohol) and poly(hydroxyethyl methyl acrylate).

While according to U.S. Pat. No. 4,582,875 the contemplated carriers may be either water soluble or water insoluble, they are clearly polymeric in nature. The activated polymeric carriers of this patent would thus not be suitable for use as cross-linking agents, where structural or configurational limitations imposed by the materials to be cross-linked would effectively preclude the use of such high molecular weight materials.

It is an object of the present invention to provide novel, relatively low molecular weight cross-linking agents which are suitably soluble in solvents of interest in the treatment of materials of biological and chemical interest and have reasonable half-lives in solutions varying over a wide range of pH values as commonly employed in analytical and preparative chemical methods.

It is a further object of the present invention to provide a method for the preparation of bi- and polyfunctional cross-linking agents as described above in high yield and of reasonable purity.

It is yet another object of the present invention to provide methods for covalently bonding two or more organic molecules with each other using the novel cross-linkers of the invention.

SUMMARY OF THE INVENTION

These and other objects are achieved by a novel class of cross-linking agent which comprises a monomeric organic compound having at least two hydroxyl groups each bonded to a different carbon atom, wherein said hydroxyl groups are activated by reaction with 2-fluoro-1-methylpyridinium toluene-4-sulfonate (FMP). Such cross-linking agents may be conveniently prepared by reaction with FMP in a suitable solvent followed by recovery of the resultant reaction products, e.g., via precipitation and filtration. The novel cross-linking agents have a wide variety of uses, including the interconnection of subunits of multimeric enzymes and the covalent immobilization of organic ligands to suitable carriers or supports.

DETAILED DESCRIPTION

Figure 1:
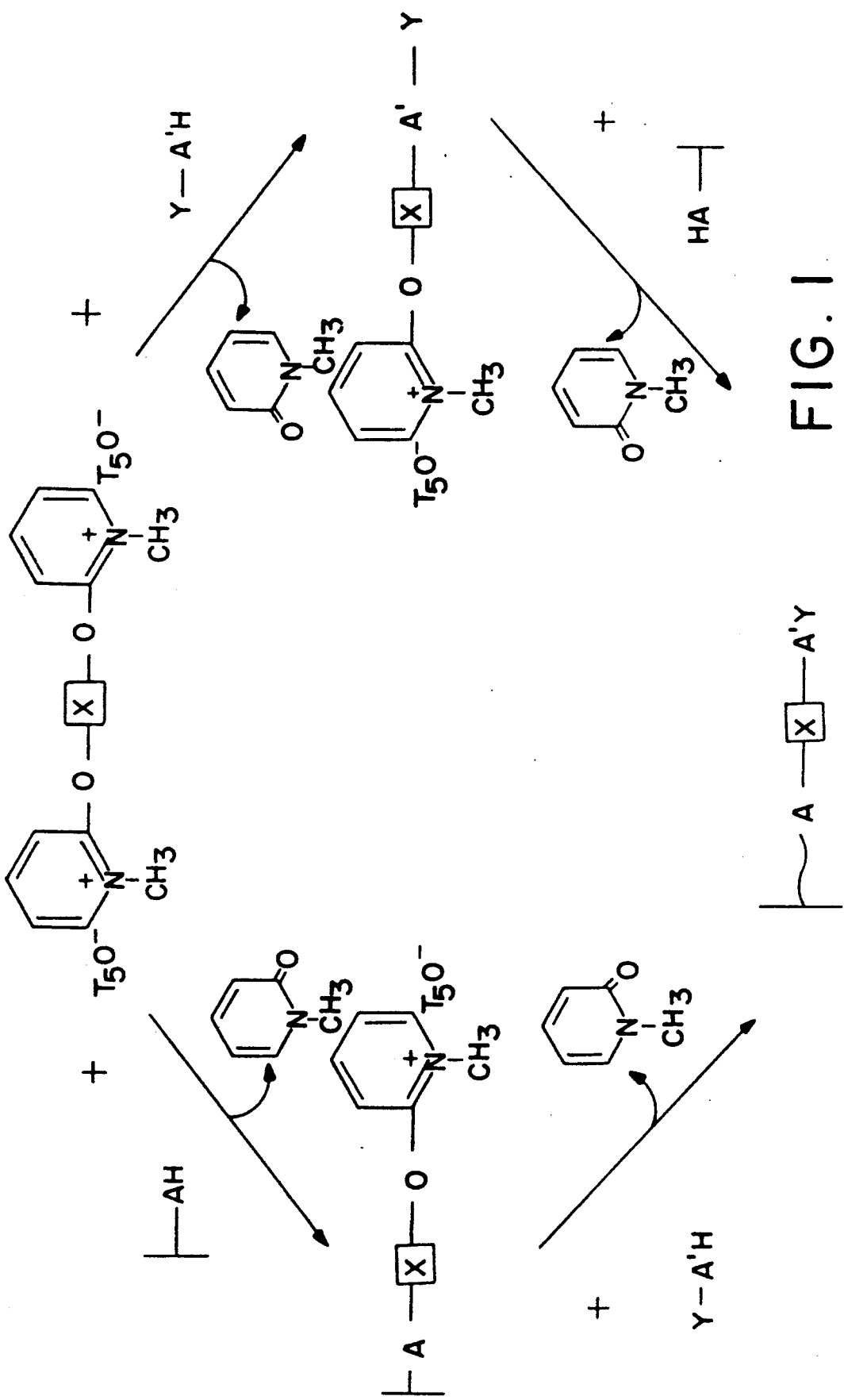
FIG. 1 is a schematic flow sheet illustrating use of the novel cross-linking agents of the invention to bind a ligand to a suitable carrier.

According to the present invention, cross-linkers may be prepared from a variety of monomeric compounds having at least two hydroxyl substituents each directly bonded to a different carbon atom (i.e., diols and polyols). For most uses, such compounds will contain no more than about twenty carbon atoms, and generally will comprise 10 carbon atoms or less. Particularly suitable monomeric compounds are alkanediols, especially primary alkanediols of the formula HO—CH$_2$—(CH$_2$)$_n$—CH$_2$—OH, in which n is an integer from 0 to 8, preferably 0 to 4. Other monomeric compounds suitable for use in preparation of the inventive cross-linkers include relatively low molecular weight polyols, such as glycerol and pentaerythritol. One class of suitable polyols may be represented by the structural formula

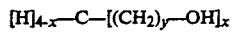

wherein x is 3 or 4 and xy is an integer less than 20. The novel cross-linkers may be suitably prepared in high yield and sufficiently pure form by reaction of the monomeric compounds with a molar equivalent of FMP per hydroxyl group to be activated in a suitable organic solvent, usually a polar solvent such as dimethylformamide or acetonitrile. Preferably, the reaction is catalyzed by a tertiary amine, such as triethylamine or tributylamine. The reaction product may be recovered by any number of procedures well known in the art. A particularly useful procedure for preparation of some compounds of the instant invention comprises precipitation of the reaction product by addition to the reaction mixture of a less polar organic solvent, such as tetrahydrofuran. In some instances, the reaction product will itself spontaneously precipitate out of solution; recovery of the spontaneous precipitate may then suitably be followed by treatment of the supernatant to recover additional product.

The novel cross-linkers may be used in a variety of different analytical and preparative contexts. According to one preferred embodiment of the invention, the cross-linkers are used to bind two or more proteinaceous materials (such as subunits of a multimeric enzyme) to one another. As the cross-linkers have relatively low molecular weights, they are particularly useful in those instances where polymeric cross-linkers either could not be used due to configurational limitations, or if used would significantly alter the conformation or other properties of the proteinaceous materials after the cross-linking reaction.

According to another preferred embodiment of the invention, an organic ligand containing at least one substituent selected from the group consisting of primary amino, secondary amino and sulfhydryl is covalently bonded to a suitable solid carrier or support by means of the cross-linkers of the invention. Unlike the polymers employed as the carriers of U.S. Pat. No. 4,582,875, which must contain at least one free hydroxyl group, according to the present invention suitable carriers contain primary or secondary amino and/or sulfhydryl functional groups. Exemplary carriers include AH-Sepharose 4B and Thiopropyl Sepharose 6B from Pharmacia, Pisctaway, N.J.; and Aminoethyl Bio-Gel P-2, Aminoethyl Bio-Gel P-100 and Affi-Gel 102 from Bio-Rad, Richmond, Calif.

As illustrated in FIG. 1, the binding of a suitable organic ligand (generically described as Y-A'H, wherein A'=—NH—, —NR— or —S—; and Y and R are independently selected from the group consisting of alkyl, aryl, acyl, etc.) may proceed by one of two reaction pathways, exemplified in FIG. 1 with respect to attachment thereof to a suitable carrier or support. According to a first pathway (left side of FIG. 1), the cross-linker is first reacted with the carrier or support (generically described as |—AH, wherein A=—NH—, —NR'— or —S—; |—=the polymeric backbone of the carrier or support; and R' =alkyl, aryl, acyl, etc.), to provide an intermediate product with an available activated hydroxyl function. This intermediate is then reacted with the ligand to provide the desired product. According to the other pathway illustrated (right side of FIG. 1), the order of reaction is reversed; i.e., the cross-linker is first reacted with the ligand, followed by reaction of an available activated hydroxyl function of the resultant intermediate with the carrier or support.

Activation of the hydroxyl functions of alkane diols or other soluble materials containing at least two hydroxyl groups with FMP provides a convenient route for synthesizing homobifunctional or polyfunctional cross-linkers which are highly soluble in aqueous media, due to the presence of the pyridinium moiety. Furthermore, the activated groups exhibit prolonged half-lives at a wide range of pH values (pH 2-10). These are highly desirable properties for cross-linking reagents.

The invention will be better understood by reference to the following examples which are intended for purposes of illustration and are not to be construed as in any way limiting the scope of the present invention, which is defined in the claims appended hereto.

EXAMPLES

All the organic solvents used in the following Examples were purchased from Aldrich Chemicals (Milwaukee, Wis.) The glass-distilled dimethylsulfoxide and the alkane diols were obtained from Fluka Fine Chemicals (Ronkonkoma, N.Y.). Sephadex G-25 Fine was purchased from Sigma Chemical Company (St. Louis, Mo.) Lactate dehydrogenase used in the cross-linking experiments was purchased from Boehringer Mannheim (Indianapolis, Ind.).

EXAMPLE 1

Preparation of 2-Fluoro-1-methylpyridinium Toluene-4-sulfonate Activated Alkanediols Two millimoles of 2-fluoro-1-methylpyridinium tosylate (FMP) were dissolved in 15 ml dimethylformamide (DMF) or in 20 ml acetonitrile in 500 ml round bottom flasks. Prior to use, all solvents used were dried for at least 48 hours using molecular sieves. One millimole of alkanediol was added to the reaction mixture, followed by 2.2 millimole of triethylamine. The flasks were closed with a glass stopper and the reaction was allowed to continue for 20 hours at room temperature. Enough tetrahydrofuran was added to the reaction mixture (approximately 200 ml) to precipitate the product. In some instances, crystallization or precipitation of the product was observed in the reaction mixture after 20 hours incubation; in such cases, the supernatant was removed and a further recovery of the product effected by further precipitation with tetrahydrofuran. The precipitate was washed with 10 ml acetone each 3 times and dried under vacuum. The final product was stored tightly closed in a glass tube at room temperature.

The above procedure was used in successfully activating the following alkane diols with FMP: (a) ethylene glycol, (b) 1,3-propanediol, (c) 1,4-butanediol, (d) 1,5-propanediol and (e) 1,6-hexanediol. Characterization of the cross-linkers was performed using the following parameters: melting points; Rf values obtained after performing thin layer chromatography on silica-coated glass plates using acetonitrile as a solvent; elemental analysis; and UV-visible spectroscopy. Table 1 shows the melting points and Rf values of the 5 cross-linkers; these parameters were found to be different in every case from FMP. Table 2 reports the results of elemental analysis for each of the cross-linkers and compares them with theoretical values. As shown in Table 2, the theoretical and the observed values are in very close agreement, confirming that the desired reaction products were obtained.

Figure 2A:
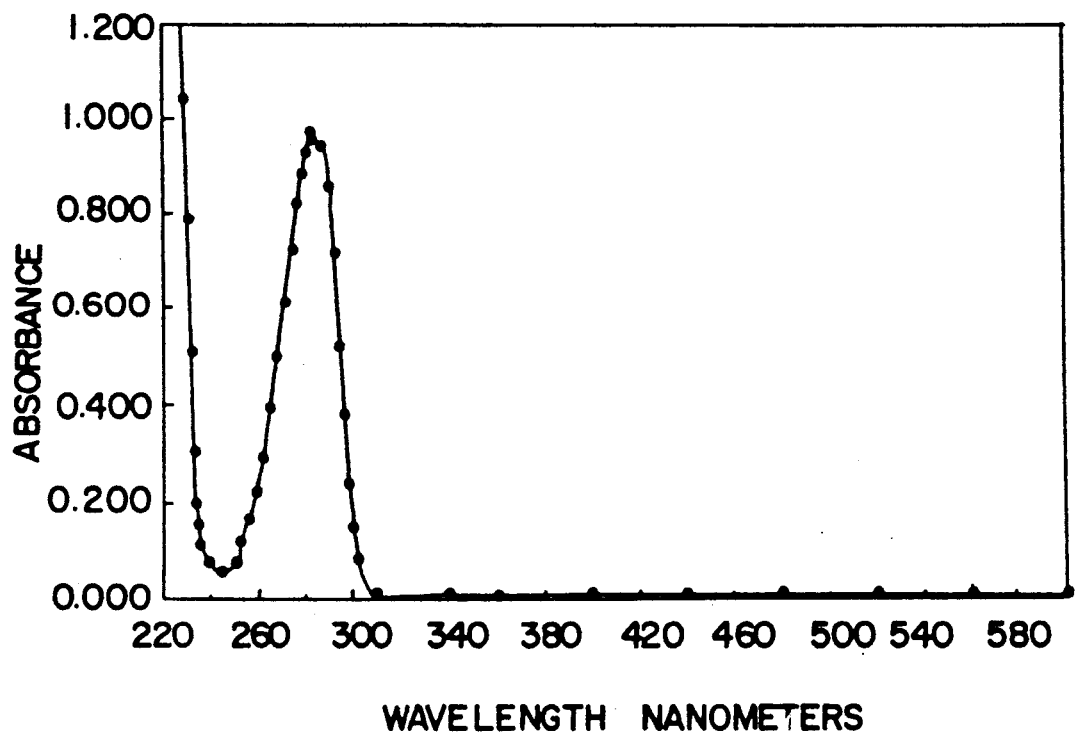
FIGS. 2(A) and 2(B) are UV-visible spectra of a novel cross-linking agent (activated hexanediol) in accordance with the invention, taken in 0.01M HCl and 0.25M NaOH solutions, respectively.
Figure 2B:
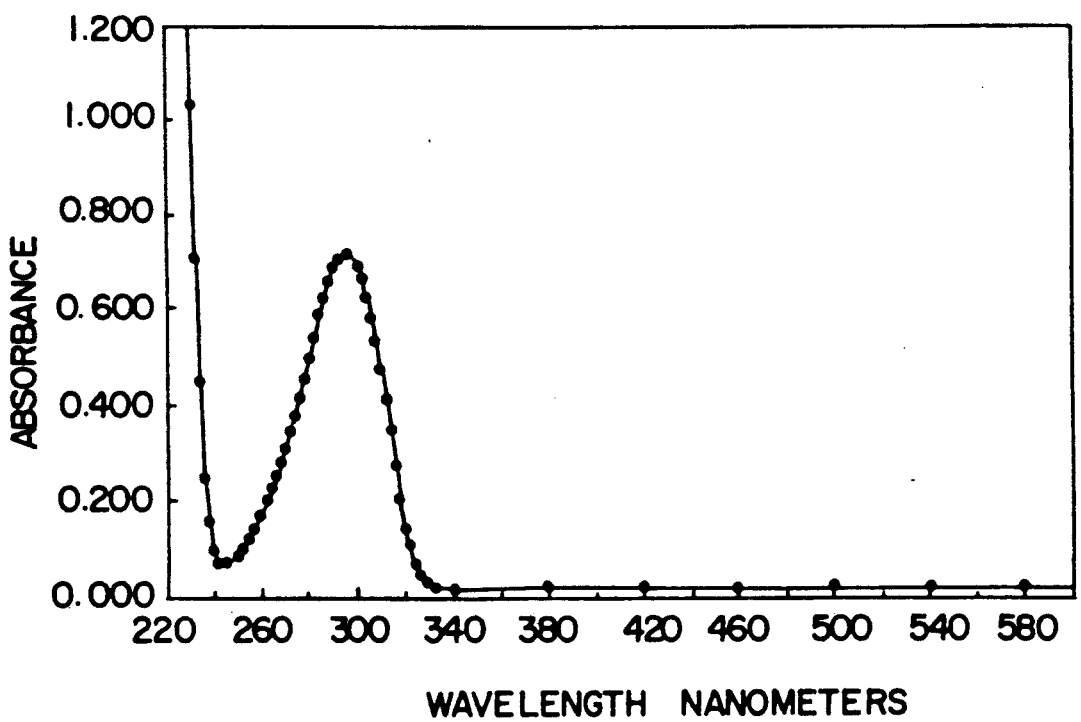

FIGS. 2(A) and 2(B) show the UV-visible spectra of one of the cross-linkers (activated hexanediol) taken in 0.01M HCl and 0.25M NaOH solution, respectively. In HCl, a peak was observed at 280 nm. Under alkaline conditions (0.25M NaOH) an absorption maximum at 297 nm was observed, this being identical to the spectrum of 1-methyl-2-pyridone (MPD). The other four cross-linkers showed comparable spectral characteristics, again confirming that the desired reaction had occurred.

EXAMPLE 2

Preparation of 2-fluoro-1-methyl pyridinium toluene-4-sulfonate Activated Alkane Polyols Exemplified by Activation of Pentaerythritol Pentaerythritol [2,2-bis(hydroxymethyl)-1,3-propanediol] contains 4 primary hydroxyl groups which can be activated with FMP, leading to a tetrafunctional cross-linking agent. Activation of pentaerythritol was carried out using the same general procedure described for the various alkanediols. Two millimole of pentaerythritol and 8 mmole of FMP were dissolved in 30 mL of dimethylformamide. To the reaction mixture, 8.8 mmole of triethylamine was added, mixed well and allowed to incubate at room temperature for 20 hours. About 200 ml of tetrahydrofuran was added to the reaction mixture to precipitate the product, which was then washed 3 times with 10 ml each of acetone and dried under vacuum. The final product was stored in a tightly closed glass tube at room temperature. The melting point of the product and the Rf values after TLC on silica gel with acetonitrile as the solvent were determined. The results are presented in Table 1.

TABLE 1

Melting Points and Rf Values of FMP Activated Alkane Diols

| Compound | Melting Point (°C.) | Rf* |
|---|---|---|
| FMP | 130-133 | 0.18 |
| Activated Ethylene Glycol | 133-136 | 0.035 |
| Activated Propanediol | 160-162 | 0 036 |
| Activated Butanediol | 158-162 | 0.039 |
| Activated Pentanediol | 160-161 | 0.038 |
| Activated Hexanediol | 168-170 | 0.053 |
| Activated Penta-Erythritol | 246-250 | 0.03 |

*Rf values were obtained after performing thin layer chromatography on silica glass plates with acetonitrile as a solvent.

TABLE 2

Elemental Analysis of FMP Activated Alkane Diols

| Compound | % C A* | % C T# | % H A | % H T | % N A | % N T | % S A | % S T | % O A | % O T |
|---|---|---|---|---|---|---|---|---|---|---|
| FMP-Activated Ethylene Glycol | 54.26 | 57.13 | 5.79 | 5.48 | 4.55 | 4.76 | 11.26 | 10.89 | 24.22 | 21.74 |
| FMP-Activated Propanediol | 57.49 | 57.79 | 5.67 | 5.69 | 4.61 | 4.65 | 11.11 | 10.64 | 21.45 | 21.24 |
| FMP-Activated Butanediol | 57.61 | 58.42 | 5.85 | 5.88 | 4.30 | 4.54 | 10.72 | 10.40 | 21.26 | 20.75 |
| FMP-Activated Pentanediol | 58.86 | 59.03 | 5.97 | 6.07 | 4.42 | 4.44 | 10.50 | 10.17 | 20.76 | 20.29 |
| FMP-Activated Hexanediol | 59.30 | 59.76 | 6.33 | 6.26 | 4.25 | 4.35 | 9.91 | 9.96 | 19.80 | 19.87 |

*A = actual analytical value
T = theoretical calculated value

EXAMPLE 3

Cross-linking of Lactate Dehydrogenase Subunits with FMP-activated Alkanediols In order to establish that the cross-linkers prepared were functional, cross-linking experiments were performed with a multimeric enzyme, lactate dehydrogenase [E.C.1.1.1.27], which comprises four identical subunits, each with a molecular weight of 35,000 daltons. Lactate dehydrogenase obtained from Boehringer Mannheim as a suspension in 2.1M ammonium sulfate was desalted by passing two times through Sephadex G-25 centrifugal columns equilibrated with 0.05M NaHCO$_3$, pH 8.5.

Approximately 2 nanomoles of the enzyme in 50 μl of 0.05M NaHCO$_3$ buffer, pH 8.5, was reacted with a 1000 fold excess (2 μmole) of the various cross-linkers at room temperature for 4 hours. At the end of the incubation, an equal volume of a buffer containing 20 mM Tris, 2 mM EDTA, 10% BME and 2.5% SDS was added to the reaction mixture. The mixture was boiled for 5 minutes and subjected to polyacrylamide gradient gel electrophoresis using the Pharmacia Phast System.

Figure 3:
FIGS. 3 and 4 illustrate the electrophoretic patterns obtained after reaction of lactate dehydrogenase with various cross-linkers in accordance with the present invention, together with suitable control samples and molecular weight standards.

FIG. 3 shows the electrophoretic pattern obtained after the reaction of the enzyme with the cross-linkers. In FIG. 3, lanes 1 and 2 are molecular weight standards. Lane 3 is the control enzyme preparation without cross-linker. Lanes 4-8 correspond to the LDH enzyme reacted with activated ethylene glycol, propanediol, butanediol, pentanediol and hexanediol, respectively. Bands a, b and c correspond to monomer, tetramer and multimers.

All compounds prepared were able to cross-link the subunits of lactate dehydrogenase. Analysis of the molecular weights of the cross-linked protein bands showed the formation of mainly tetramers and multimers, high molecular weight species which do not migrate into the gel. The results clearly indicate that the cross-linkers prepared by the method described are functional and are able to cross-link subunits of multimeric proteins.

EXAMPLE 4

Cross-linking of Lactate Dehydrogenase Subunits with FMP-activated Alkane Polyols Approximately 2 nmoles of the enzyme in 50 μl of Na$_2$B$_4$O$_7$ buffer 0.05M, pH 8.5, was mixed with 100, 200 or 500 fold excess of FMP-activated pentaerythritol, or a 500 fold excess of FMP-activated butanediol, pentanediol or hexanediol, for comparison. After incubating the mixture for four hours, an equal volume of a buffer containing 20 mM Tris, 2 mM EDTA, 10% 2-mercaptoethanol and 2.5% SDS was added. The reaction mixture was boiled and subjected to polyacrylamide gel electrophoresis using the Pharmacia-LKB Phast system.

Figure 4:
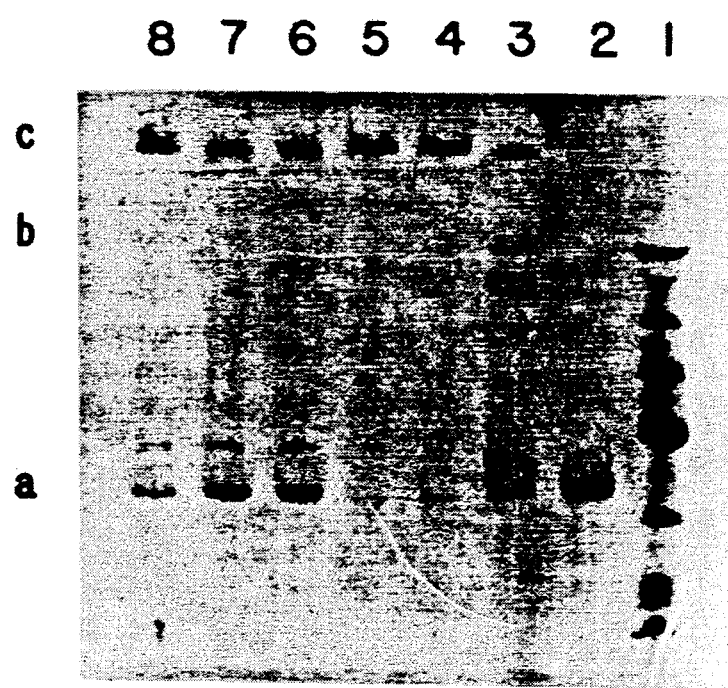

FIG. 4 shows the electrophoretic pattern for various materials as hereinafter described. Lane 1 contains molecular weight standards and lane 2 contains control lactate dehydrogenase without any crosslinker. Lanes 3, 4 and 5 contain the products of lactate dehydrogenase cross-linking experiments performed respectively with activated butanediol, pentanediol and hexanediol while lanes 6, 7 and 8 contain the products of analogous cross-linking experiments performed with activated pentaerythritol at 100, 200 and 500 fold excess of the cross-linker, respectively. At different concentrations, activated pentaerythritol gave mainly two bands, one corresponding to the highly cross-linked high molecular weight multimers (band c) and some unreacted monomers (band a). Increasing the concentration of the cross-linker seemed to increase the proportion of the high molecular weight band (lane 8), as shown by its intensity. The FMP-activated pentaerythritol used in this experiment was able to cross-link the enzyme as shown by the electrophoretic pattern. Under the conditions used, activated butanediol yielded protein bands corresponding to some tetramers (lane 3, band b) and high molecular weight polymers (band c) which do not migrate into the gels. Some amount of uncross-linked monomers were also present with this cross-linker (band a). Cross-linking with both activated pentanediol and hexanediol resulted mainly in high molecular weight nonmigrating bands (lanes 4 and 5, band c) with small amounts of unreacted monomers (band a). The results presented here clearly show that the FMP-activated pentaerythritol is able to function as a protein cross-linking agent, similar to the FMP-activated alkanediols.

EXAMPLE 5

Immobilization of $^{125}$I-labelled Bovine Serum Albumin (BSA) on Aminohexyl Sepharose by Simultaneous Addition of Cross-linker and Protein to the Gel One gram (approximately 4 ml) of aminohexyl Sepharose (AH-Sepharose, Pharmacia-LKB) was added to 20 ml of 0.5M NaCl and allowed to swell for about 2 hours. The gel was then washed with 50 ml of 0.5M NaCl and 50 ml of 0.05M Na$_2$B$_4$O$_7$ buffer pH 8.5. In each of 3 propylene tubes, 0.5 ml of the gel (approximately 7 μmoles of amino groups) was pipetted out, the material centrifuged at 1500 rpm for 2 minutes and the supernatant buffer removed. To each of the tubes containing the gel, a 1 ml solution of labelled BSA (9.2 mg/ml, 2.38×10$^6$ cpm) was added and the contents of the tubes mixed. To the first tube, which served as a control, 1 ml of 0.05M borate buffer was added; to each of the remaining two tubes, 1 ml of a 70 mM solution of FMP-activated hexanediol in borate buffer (70 μmoles, amounting to a 10-fold excess over the amino functions) was added. After mixing, the contents of the tubes were tumbled at room temperature for 18 hours. The tubes were then centrifuged and the supernatants removed. The gels were successively washed with 10 ml each of 0.05M borate buffer, 0.5M NaCl, water and 0.05M borate buffer. The wash cycles were repeated 3 times and the gels were counted for $^{125}$I using a Beckman Gamma 5500 counter. Radioactivity bound to the control gel was subtracted from that bound to the experimental gels. The amount of $^{125}$I BSA bound to the gels was determined to be 4.56±0.06 mg/ml gel.

EXAMPLE 6

Immobilization of $^{125}$I labelled BSA after Preactivation of AH-Sepharose with FMP-activated hexanediol AH-Sepharose washed as described in Example 5 was used. In each of 2 polypropylene tubes 0.5 ml of the gel was pipetted out and 1 ml of a 700 mM solution of FMP-activated hexanediol (100-fold excess over the amino functions) was added to the tubes. The reactants were mixed by tumbling at room temperature for 20 minutes, following which excess cross-linker was removed from the gel by washing first with 10 ml each of 0.001N HCl and then with 10 ml of borate buffer. To the activated gel, 1 ml of the $^{125}$I labelled BSA was added. The control gel in Example 5 served as a control in this example as well. After allowing the gels to tumble at room temperature, they were processed as described in Example 5 and the $^{125}$I BSA bound was determined by counting the gels in the Beckman Gamma counter. $^{125}$I BSA binding capacity was 5.17±0.18 mg/ml.

EXAMPLE 7

Immobilization of $^{125}$I Labelled BSA after Preactivation of Aminoethyl Gel with FMP-activated hexanediol One-half gram of Biogel P2 (BioRad Laboratories; approximately 8 ml) was added to 10 ml of 0.05M borate buffer and allowed to stand for 2 hours and the swollen gel was washed with 50 ml of the borate buffer. The amino functions on the gel (0.5 ml containing approximately 70 μmoles of amino groups) were preactivated according to the procedure described in Example 6, except that a 40-fold excess of the cross-linker was used. As a control, 0.5 ml gel to which only one borate buffer was added in the activation step was used. After counting the $^{125}$I-BSA attached to the gel, the binding capacity was determined to be 1.74±0.22 mg/ml gel.

EXAMPLE 8

Immobilization of $^{125}$I Labelled BSA after Preactivation of Sulfhydryl Gel with FMP-activated hexanediol Affigel 401 (BioRad Laboratories) was supplied as a suspension in buffer solution. About 2 ml of the gel was washed with borate buffer and 0.5 ml (approximately 3 μmoles of sulfhydryl groups) each dispensed into 3 separate tubes. A first tube was used as a control; to each of the remaining 2 tubes, 1 ml of 300 mM FMP-activated hexanediol (100-fold excess over sulfhydryl groups) in borate buffer was added. The reaction and the coupling of $^{125}$I labelled BSA was carried out as described in Example 6. After corrections were made for the controls, the $^{125}$I labelled BSA was determined to be 0.82±0.15 mg/ml gel.

What is claimed is:

1. A method of cross-linking at least two organic molecules each with at least one substituent independently selected from the group consisting of primary amino, secondary amino and sulfhydryl, said method comprising reacting said at least two organic molecules with a cross-linker which comprises a monomeric organic compound having at least two hydroxyl groups each bound to a different carbon atom, said at least two hydroxyl groups having been activated by reaction with 2-fluoro-2-methylpyridinium toluene-4-sulfonate.

2. A method according to claim 1, wherein said monomeric organic compound is a diol having a structural formula of HO—H$_2$C—(CH$_2$)$_n$—CH$_2$—OH, wherein n =0 to 18.

3. A method according to claim 2, wherein said diol is selected from the group consisting of ethylene glycol, propanediol, butanediol, pentanediol and hexanediol.

4. A method according to claim 1, wherein said monomeric organic compound is a polyol of 3 to 20 carbon atoms.

5. A method according to claim 1, wherein said polyol is glycerol or pentaerythritol.

6. A method according to claim 1, wherein each of said at least two organic compounds is independently selected from the group consisting of proteins, amino acids and nucleic acids.

* * * * *